Figure 1:
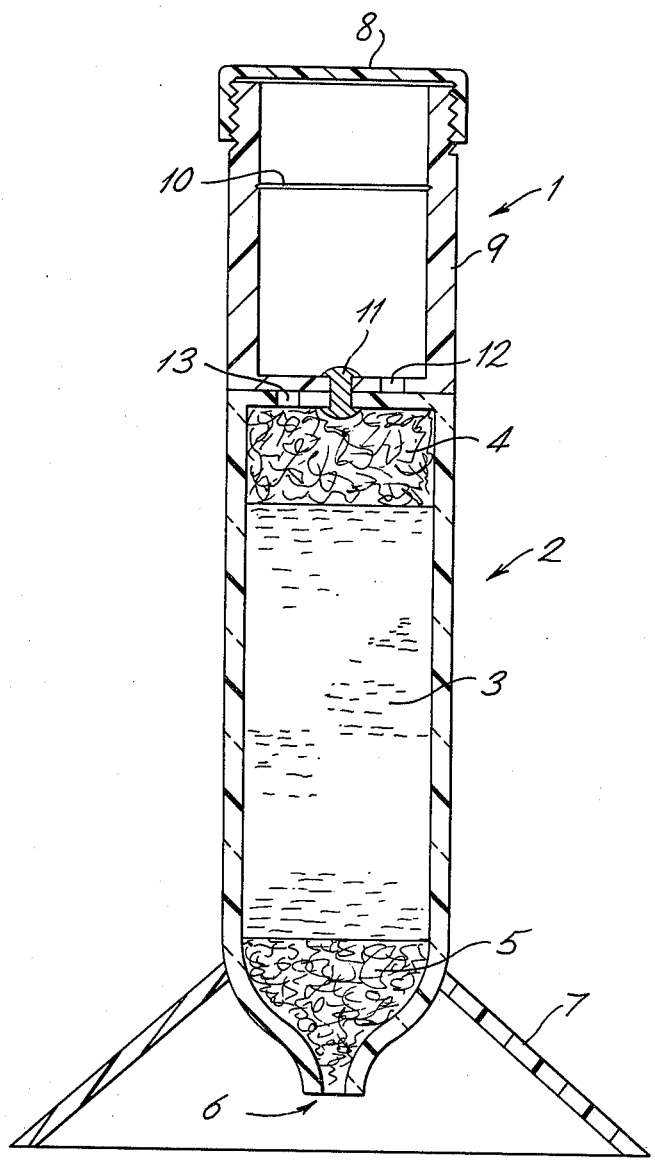

United States Patent [19]

Richardson et al.

[11] 4,318,986

[45] Mar. 9, 1982

[54] ENZYME ASSAYS

[75] Inventors: Anthony C. Richardson, Henley-on-Thames; Perry F. G. Praill, Uxbridge; Robert G. Price, Northwood, all of England

[73] Assignee: National Research Development Corporation, London, England

[21] Appl. No.: 127,242

[22] PCT Filed: Oct. 31, 1978

[86] PCT No.: PCT/GB78/00033

§ 371 Date: Jun. 29, 1979

§ 102(e) Date: Jun. 29, 1979

[87] PCT Pub. No.: WO79/00255

PCT Pub. Date: May 17, 1979

[30] Foreign Application Priority Data

Nov. 1, 1977 [GB] United Kingdom ............... 45390/77

[51] Int. Cl.$^3$ .............................................. C12Q 1/34
[52] U.S. Cl. ........................................ 435/18; 435/19; 435/20; 435/21; 435/22; 435/23; 435/24; 435/288; 435/299; 435/300; 435/805; 435/806; 435/810
[58] Field of Search ...................... 435/18, 19, 20, 21, 435/22, 23, 24, 288, 296, 299, 300, 301, 805, 806, 810

[56] References Cited

U.S. PATENT DOCUMENTS

| | | | |
|---|---|---|---|
| 3,410,756 | 11/1968 | Guibault et al. | 435/18 X |
| 3,616,251 | 10/1971 | Linoli | 435/18 X |
| 3,875,013 | 4/1975 | Manautou et al. | 435/18 |
| 3,968,011 | 7/1976 | Manautou et al. | 435/18 |
| 4,039,388 | 8/1977 | Gal et al. | 435/21 |
| 4,082,781 | 4/1978 | Gal | 435/21 X |
| 4,223,090 | 9/1980 | Mazza | 435/19 |

FOREIGN PATENT DOCUMENTS 2358419 2/1978 France .
1172050 11/1979 United Kingdom .

OTHER PUBLICATIONS

Chemical Abstracts, vol. 86, 166848h; 1977.
Dictionary of Organic Compounds, V. 3, pp. 1767–1768.
Dictionary of Organic Compounds, V. 4, p. 2469.
Dictionary of Organic Compounds, V. 4, p. 2471.

*Primary Examiner*—Robert J. Warden
*Attorney, Agent, or Firm*—Oblon, Fisher, Spivak, McClelland & Maier

[57] ABSTRACT

An enzyme assay reagent comprises a substance which is capable of interaction with the enzyme to give rise to the formation of a compound of formula X—A—Y—NO$_2$, wherein A comprises an aromatic nucleus, X comprises an auxochromic group and Y comprises an unsaturated group which is capable of transmitting electron resonance between the aromatic nucleus and the nitro substituent, said compound per se being capable of producing a visual signal which is easily discernible by eye.

22 Claims, 2 Drawing Figures

U.S. Patent   Mar. 9, 1982   Sheet 1 of 2   4,318,986

ENZYME ASSAYS

This invention relates to enzyme assays, and in particular to reagents for the detection and determination of enzymes.

The presence or absence of certain enzymes in physiological samples, such as urine or serum samples from human patients, is a valuable indicator of illness or deficiencies in the organism concerned e.g. organ malfunctions in human patients. For example, increases in the level of the enzyme N-acetyl-$\beta$-D glucosaminidase (NAG) excreted in the urine of "kidney transplant" patients is an early sign of impending rejection of the transplanted kidney, besides being a general indicator of renal and other diseases. At present the customary clinical assay for NAG involves incubation of a sample of urine with the 4-methylumbelliferyl glycoside substrate of the enzyme which interacts to release the corresponding umbelliferone which is then monitored fluorimetrically. Alternatively, a nitrophenyl glycoside substrate, p-nitrophenyl-2-acetamido-2-deoxy-$\beta$-D-glucopyranoside, may be used, interacting with the enzyme to release p-nitrophenol which is monitored colorimetrically. Both these assays, however, require the use of sophisticated spectrophotometric apparatus and thus are only suitable for use when there is access to well-equipped laboratory facilities.

New enzyme assay reagents have now been devised which, in some cases, may be employed without requiring the use of sophisticated monitoring apparatus.

According to the present invention an enzyme assay reagent comprises a substance which is capable of interaction with the enzyme to give rise to the formation of a compound of formula X—A—Y—NO$_2$, wherein A comprises an aromatic nucleus, X comprises an auxochromic group and Y comprises an unsaturated group which is capable of transmitting electron resonance between the aromatic nucleus and the nitro substituent, said compound per se being capable of producing a visual signal which is easily discernible by eye.

The invention also includes a method for the assay of an enzyme which comprises incubating a sample containing the enzyme with a reagent according to the invention to give rise to the production of a compound of formula X—A—Y—NO$_2$ as hereinbefore defined, and, if necessary, subjecting the compound to further treatment to develop a visual signal which is easily discernible by eye.

The reagent typically comprises an enzyme substrate portion and a further portion which gives rise to the formation of the compound of formula X—A—Y. Usually the reagent of the invention comprises the compound X—A—Y—NO$_2$, or a simple precursor therefor, in combination with the substrate portion, and on interaction with the enyzme the substance releases the compound or simple precursor. Thus the compound or precursor is usually attached to the substrate portion at or adjacent to the side within the substance at which enzyme activity takes place. In one embodiment the enzyme substrate portion and further portion of the reagent are conveniently linked through the auxochromic group X and the substance has the general formula S—X—A—Y—NO$_2$, wherein S comprises the enzyme substrate portion of the substance and X, A and Y are as previously defined, and such reagents release the compound on intereaction with the enzyme.

The reagents, substances and method of the present invention are widely applicable to the assay of enzymes in general, the enzyme substrate portion of the substance being varied in accordance with the particular enzyme which it is desired to assay. Typically, however, the enzymes which may be assayed by the invention are catabolic enzymes, such as those which play an important role in the breakdown of macromolecules in cellular tissues. For example, enzymes which may be assayed include carboxylate esterases and lipases, acid and alkaline phosphatases, phosphodiesterases and sulphatases, and thus corresponding reagents may comprise appropriate carboxylate, phosphate, diphosphate and sulphate esters. Also, in particular, the invention is applicable to the assay of glycosidases in which case the substrate portion S of the reagent characteristically comprises a corresponding glycoside carbohydrate substituent, such as an $\alpha$ or $\beta$-glucopyranosyl, -galactopyranosyl, or -mannopyranosyl substituent. For example, the invention has been found to be particularly suitable for application to the assay of N-acetyl-$\beta$-D-flucosaminidase (NAG).

The invention may be employed to assay for the presence of enzymes in general and to monitor their concentration levels; for instance, for diagnosis of a corresponding defect or illness. For example, the NAG content of urine may be assayed for early detection of kidney disease, or in the specific case as an early indicator of kidney rejection in "kidney transplant" patients. Alternatively, the invention may be used to determine the absence of enzymes which may, for instance, be indicative of certain genetic disorders. Generally, also, the reagents and method of the invention may provide convenient tools for use in biochemical and medical research.

Preferably the compound X—A—Y—NO$_2$ is capable of producing a colour change which is easily discernible to the eye, and in this latter respect the colour produced is typically substantially different from background colouration of the sample. For example, reagents of the invention for use with urine samples, such as reagents for assay of NAG, typically release substances capable of producing colours substantially different from the background colour of urine. Preferably the reagents of the invention release compounds which are capable of producing distinctive colours, preferably reds or blues. Thus suitable released compounds usually have a $\lambda$ max under alkaline conditions in the range from about 450 up to about 700, preferably from about 500 up to about 600, especially in combination with a high extinction co-efficient e.g. $\epsilon$ greater than about 20,000.

It will be appreciated that within the general formula of the compounds X—A—Y—NO$_2$ there exist many typical coloured and dye compounds and suitable compounds for providing the easily discernible visual signal will be apparent to skilled workers in the art. Preferably, however, the group A comprises a monocyclic aromatic nucleus, especially a benzene nucleus.

Also the group Y may comprise any suitable unsaturated group which is capable of transmitting electron resonance between A and the NO$_2$ substituent, and may include systems containing heteroatoms and/or annulated systems. Thus, for example, the group A may comprise a benzene ring which is one ring of a naphthyl nucleus, the other ring of the naphthyl nucleus providing the group Y. Also the group Y may comprise acetylenic unsaturation. More preferably, however, the group Y comprises ethylenic unsaturation which is conjugated with respect to the aromatic nucleus A e.g. an ethenyl, butadienyl or hexatrienyl substituent. Thus in a preferred embodiment the reagent of the invention is capable of interacting with the enzyme to give rise to a compound of formula I

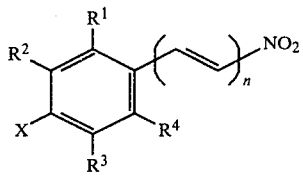

wherein X is as previously defined, n=1, 2 or 3 and $R^1, R^2, R^3$ and $R^4$=H, OMe, $NO_2$, $CH_3$, —CH=CR'R'' or $CO_2H$. The groups R' and R'' of the substituent —CH=CR'R'' may represent groups similar to $R^1$, $R^2$, $R^3$ and $R^4$, preferably H, $NO_2$ or further conjugated unsaturated substitution e.g. —CH=CR$^x$R$^y$.

The auxochromic group X may comprise any suitable auxochromic group such as an amino group ($NH_2$) or preferably a hydroxyl group (—OH).

In particularly preferred embodiments X is a hydroxyl group and A comprises a styryl group. Thus particularly preferred reagents according to the invention are those which on interaction with the enzyme give rise to the formation of a 4-hydroxy-α-nitrostyrene compound, i.e. of the formula II below,

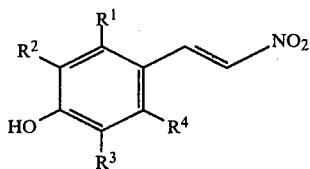

wherein $R^1$, $R^2$, $R^3$ and $R^4$ are as previously defined. The compounds of formula II in general exhibit surprising and highly desirable colour properties which make them particularly suitable for use as a component of the reagent of the invention. It has been found that the compounds of formula II are typically strongly red in colour under alkaline conditions as compared with the weak orange-yellow colour of para nitrophenol, and also that they have absorbance maxima (λ max) which are unexpectedly significantly higher than that of para nitrophenol (~400 under alkaline conditions). It is now believed that these enhanced colour properties are due to the formation of a radical ion resulting from an oxidative process, as shown below

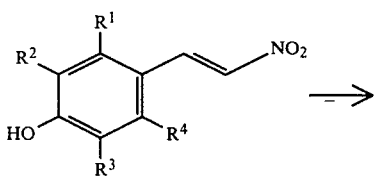

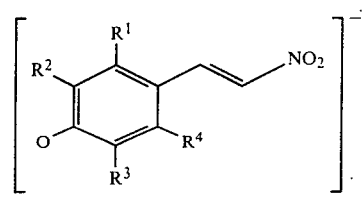

The existence of electron donating substituents, such as alkoxy groups e.g. methoxy, adjacent to the hydroxyl substituent appears to stabilise the formation of this radical ion, as is borne out by the colour properties of the 3-methoxy and especially the 3,5-dimethoxy analogues shown below as formulae III and IV respectively, upon which particularly preferred reagents are based.

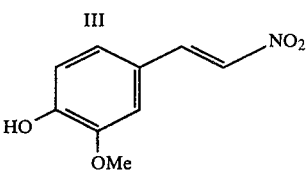

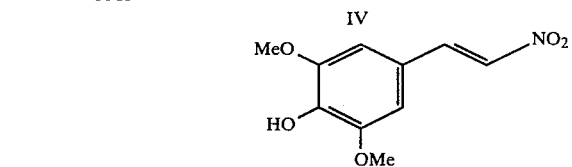

Thus the mono-methoxy compound III and the dimethoxy compound IV have absorbance maxima (λ max) of 506 and 530 with extinction co-efficients (ε) of 24,600 and 22,300 respectively in buffer at pH 8.8, and exhibit satisfactory scarlet-red colourations under these conditions.

Conveniently the auxochromic group X e.g. —OH, may provide the linkage between the compound X—A—Y—$NO_2$ and the substrate portion of the reagent, such that the compound is released on interaction with the enzyme. Thus examples of reagents according to the invention are given below by formulae A to E, referring, for the sake of simplicity, only to reagents comprising a simple 4-hydroxy-ω-nitrostyryl substituent. It will be appreciated, however, that this latter substituent may be replaced by a substituent relating to the compounds X—A—Y—$NO_2$ in general.

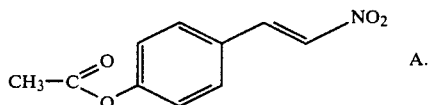

A.

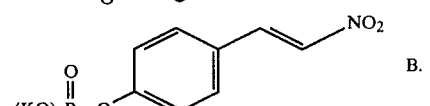

B.

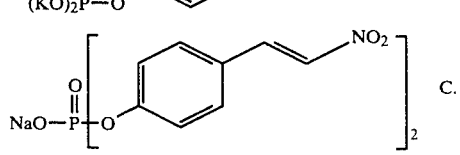

C.

-continued

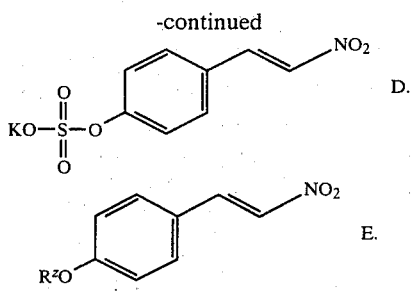

The aforementioned reagents A–E are reagents suitable for assay of (A) esterases or lipases, (B) acid or alkaline phosphatases, (C) phosphodiesterases, (D) arylsulphatases and (E) glycosidases respectively. $R^z$ in formula E denotes a carbohydrate substituent, such as an $\alpha$ or $\beta$ glucopyranosyl, galactopyranosyl or mannopyranosyl In accordance with the invention, it has been found that the preferred nitrostyryl substituted reagents may be prepared from vanillin or similar hydroxy benzaldehyde based materials such as p-hydroxybenzaldehyde or salicylaldehyde by nitromethylation of the corresponding substrate-vanillin or -similar compound adduct. Preferably mildy alkaline conditions are employed during nitromethylation. It is believed that similar reagents may be prepared by correspondingly similar routes.

Samples which may be assayed are conveniently in fluid form and include samples comprising physiological fluids, such as serum or urine. Other suitable samples may also be assayed including samples derived from cell homogenates, such as those samples commonly used in the study of genetic disorders.

The reagent and sample are incubated together; for instance, sample and solution containing the reagent are mixed and allowed to interact under appropriate conditions for a suitable period of time. Preferably the temperature used during incubation is greater than about 30° C. e.g. from about 30° up to about 40° C., and under these conditions an incubation period of up to about thirty minutes e.g. from about 10 to 15 up to about thirty minutes, is usually satifactory. As an alternative to the use of reagent in solution, the reagent may be used in association e.g. absorbed, with a suitable solid phase material, such as cellulose particles, e.g. microcrystalline cellulose, which may advantageously overcome problems arising from the insolubility or poor solubility of the reagent. Also the reagent may be used in association with a porous solid support material, such as paper, to provide a convenient test paper or dip stick for a simple dip test. Such products comprising the reagent of the invention in association with a suitable inert solid material or with a porous solid support material are included within the scope of the invention.

On incubation the reagent releases, or more generally gives rise to the formation of, a compound which may without further treatment provide the visual signal e.g. colour, which is indicative of the presence of the enzyme in the sample. Often, however, the compound may require further treatment to develop the visual signal, and such treatment typically comprises activation to develop the inherent visual signal of the compound. This further treatment does not include steps of synthetic or preparative chemistry, such as the diazonium coupling procedures employed with some prior art enzyme assay reagents. Commonly the treatment comprises alkaline treatment, which may lead to salt formation permitting delocalisation of electronic charge, for instance, alkaline treatment of preferred conjugated unsaturated chromophore substances advantageously giving rise to the development of coloured visual signals. Alkaline treatment may comprise addition of alkali to solution containing the released compound, or preferably solution containing the compound is brought into contact with a solid phase reagent e.g. an absorbent, which simultaneously presents an alkaline environment to the compound. For example, the solution containing the compound is contacted with an anionic exchange material, which is preferably of neutral colour e.g. white or light-coloured, and which is in its free base form e.g. hydroxyl (OH$^-$) form. For example, the anionic exchange material may comprise DEAE cellulose, or a similar light coloured anion exchange material in free base form. The use of an absorbent anionic exchange material may be particularly advantageous, absorbing and concentrating the released substance into a narrow band for enhanced ease of monitoring. The use of DEAE cellulose and similar materials, in this latter respect is believed to be novel, and this use, in general, of these materials is included within the scope of the invention.

In a preferred embodiment, therefore, the method of the invention comprises incubating sample comprising the enzyme with reagent associated with solid phase material e.g. an inert absorbent or a porous support material, so as to give rise to the formation of a compound X—A—Y—NO$_2$, and contacting solution containing the compound with a solid phase reagent which presents an alkaline environment to the substance and thereby produces a colour change or other visual signal which is easily discernible by eye.

There is also provided apparatus for carrying out the method of the preferred embodiment usually in the form of a through-flow device normally comprising two compartments, an incubation compartment containing reagent associated with solid phase material, e.g. microcrystalline cellulose, and a visualisation compartment containing a solid phase reagent which presents an alkaline environment to the substance e.g. DEAE cellulose or a similar substance. The compartments are typically interconnectable e.g. by a suitable connecting passageway, to permit flow of liquid containing the released compound from the incubation to the visualisation compartment. The two compartments are preferably, however, capable of isolation from one another, for instance to allow for retention of the sample in the incubation compartment for the required incubation period. The passageway between the two compartments may be provided with an appropriate tap or other barrier which may be conveniently opened or removed after the required incubation period to permit the liquid to pass into the visualisation compartment e.g. to pass through the preferred DEAE cellulose absorbent.

For example, the through-flow device may consist of two compartments attached at interfacial surfaces by a pivot, both surfaces provided with outlets at a fixed radius from the pivot such that mutual rotation of the compartments brings the outlets into coincidence with one another providing a passageway between the compartments. Alternatively the passageway between the compartments may be blocked with a flimsy barrier which can be ruptured as desired, for instance by bringing the two compartments together e.g. by a screw-threaded action.

The concentration of reagent used e.g. present in association with inert solid phase material, may be varied as desired, for instance, in accordance with the threshold concentration of enzyme which it is desired to monitor; increases in concentration of reagent generally permitting detection of lower threshold concentrations of enzyme. Furthermore, use of a solid phase reagent, such as DEAE cellulose, to visualise the released substance advantageously permits detection of very small quantities of released substance, owing to concentration of the colour produced in a narrow absorbed band. In this respect, it has been found possible to detect the presence of the substance 2-methoxy-4-($\beta$-nitroethenyl) phenol at concentrations of $1-2\times 10^{-6}$ molar by contact of the solution with DEAE cellulose. Also it has been found, for example, that use of 3% of the appropriate NAG detecting glycoside (E) on an inert cellulose solid phase in combination with DEAE cellulose visualisation is capable of detecting a threshold concentration of NAG in urine from about 40-50 n mol/ml after incubation at 37° for twenty minutes; whereas, use of cellulose containing 8% of the glycoside in the same system gives a threshold of detection of about 20-30 n mol/ml. Both systems give broad intense bands for abnormal urines which are easily distinguished from those given by normal urines. It will be appreciated, therefore, having regard to the effect of substrate concentration and the ease of visualisation, that the method of the invention may be conveniently performed by patients themselves in their homes using a suitably prepared through-flow device and requires minimal analytical skills. For example, the patient may simply add a fixed quantity of fresh urine to the incubation compartment e.g. up to a fixed level indicated on the side of the compartment, and after a standard incubation period, which will usually depend upon the ambient temperature, connect the incubation and visualisation compartments permitting incubated urine to flow through the solid phase visualising reagent.

The visual signal, e.g. colour change, produced by the released substance advantageously provides a simple and quick means of detecting the presence of the enzyme in the sample as compared with the methods previously used which rely upon sophisticated monitoring apparatus. Also the intensity of the visual signal e.g. colour, produced may conveniently be used as a rough visual indicator of the concentration of enzyme present in the sample. If more accurate measurements are required, however, the reagents of the invention may be monitored spectrophotometrically, for instance in the conventional manner. For example, the colour produced may be estimated using a colourimeter, usually after adjustment of pH to 8.5-9.5 with an appropriate buffer, and, in such methods, the present reagents may be more suitable than corresponding prior art reagents, such as p-nitrophenolic and o- nitrophenolic substrates.

Figure 2:
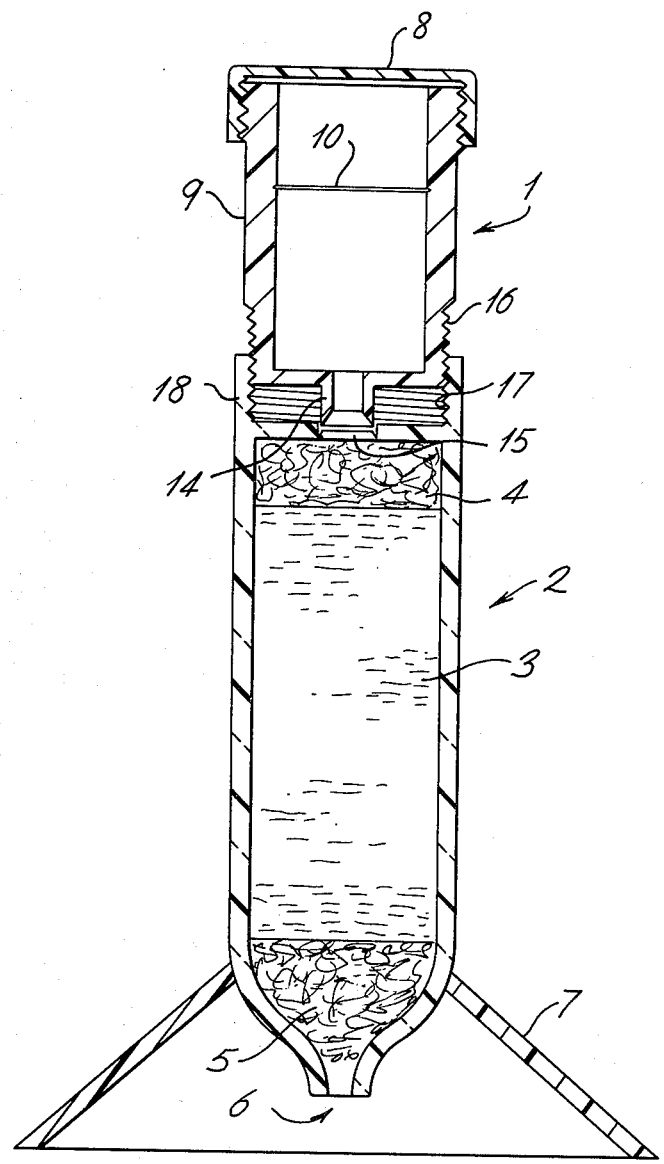

The invention is further described by way of illustration only in the following examples and description which relate to the preparation of enzyme assay reagents according to the invention and components thereof and to their use in the method of the invention, the description also referring to the accompanying diagrams in which:

FIG. 1 represents one form of flow-through device according to the invention; and FIG. 2 represents an alternative form of flow-through device according to the invention.

EXAMPLE I

Preparation of nitrostyryl glycosides for detection and determination of corresponding glycosidases I. Preparation of hydroxy-benzaldehyde glycosides As a first stage in the preparation of nitrostyryl glycoside enzyme substrates according to the invention the appropriate hydroxy-benzaldehyde glycosides are prepared.

A solution of the appropriate glycopyranosyl halide (70 mmole) in acetone (200 ml) was treated with a solution of the phenol (100 mmole) in M-sodium hydroxide, the resulting mixture being maintained at room temperature with stirring for a period of about 16 hours. The reaction mixture was then diluted with water until the product separated. Crystalline glycoside products were filtered off directly, and non-crystalline products were isolated by chloroform extraction in the usual manner.

After crystalline products have been filtered off, further product may be recovered from the mother liquors by extraction with chloroform or dichloromethane.

The results obtained during the preparation of a range of hydroxy-benzaldehyde glycosides are given below.

(a) 4-(2-acetamido-3,4,6,tri-O-acetyl-2-deoxy-$\alpha$-D-glucopyranosyloxy)-3-methoxybenzaldehyde was obtained in 55% yield from the 2-acetamido-3,4,6-tri-O-acetyl-2-deoxy-$\alpha$-D-glucopyranosyl chloride and had m.p. 220°-221° (ethanol), $[\alpha]_D - 13.5°$ (c 1, DMSO).

(b) 4-(2-acetamido-3,4,6-tri-O-acetyl-2-deoxy-$\beta$-D-glucopyranosyloxy) benzaldehyde was obtained similarly in 47% yield, $[\alpha]_D - 19°$ (c 1, CHCl$_3$).

(c) 4-(2-acetamido-3,4,6-tri-O-acetyl-2-deoxy-$\beta$-D-glycopyranosyloxy)-3,5-dimethoxybenzaldehyde was obtained similarly in 15% yield m.p. 239°-240° (methanol), $[\alpha]_D + 3.8°$ (c$_1$2 DMSO)

(d) 4-(2,3,4,6-tetra-O-acetyl-$\beta$-D-glucopyranosyloxy)-3-methoxybenzaldehyde was obtained from 2,3,4,6-tetra-O-acetyl-$\alpha$-D-glucopyranosyl bromide in 62% yield, m.p. 135°-136° (ethanol), $[\alpha]_D - 24.2°$ (c 1.1, CHCl$_3$).

(e) 4-O(2,3,4,6-tetra-O-acetyl-$\beta$-D-galactopyranosyloxy)-3-methoxybenzaldehyde was obtained from 2,3,4,6-tetra-O-acetyl-$\alpha$-D-galactopyranosyl bromide initially as a syrup (47%) which crystallised and was recrystallised with difficulty from ethanol-ether-light petroleum, m.p. 148°-149°, $[\alpha]_D - 4.4°$ (c 1.1, CHCl$_3$).

(f) 4-(2,3,4,6-tetra-O-acetyl-$\alpha$-D-mannopyranosyloxy)-3-methoxybenzaldehyde was obtained as a syrup in 14% yield from 2,3,4,6-tetra-O-acetyl-$\alpha$-D-mannopyranosyl bromide (15), $[\alpha]_D + 15.9°$ (c 1.4, CHCl$_3$).

II. O-Deacetylation of hydroxy-benzaldehyde glycosides

In the next stage of the preparation of the nitrostyryl enzyme substrates certain of the hydroxy-benzaldehyde glycosides are O-deactylated by treatment with methanolic sodium methoxide. Solutions of the acetylated glycosides (15 m mole) in methanol (50-500 ml) were treated with M-methanolic sodium methoxide (0.5-2 ml) and the solutions allowed to stand at room temperature for 20-30 minutes, or until reaction had been completed as indicated by t.l.c. determination. The solutions were then passed through pads of silica gel to remove sodium ions, and then evaporated to dryness.

The results obtained for various glycosides are given below.

(a) 4-(2-acetamido-2-deoxy-β-D-glucopyranosyloxy)-3-methoxybenzaldehyde crystallised directly from the reaction mixture in 90% yield and had m.p. 199°-200° (dec.), $[\alpha]_D -20°$ (c 1, DMSO)

(b) 4-(β-D-glucopyranosyl)-3-methoxy-benzaldehyde was obtained in 85% yield as a white powder, m.p. 188°-190°, $[\alpha]_D +2.2$ (c 0.7, DMSO)

(c) 4-(α-D-galactopyranosyloxy)-3-methoxybenzaldehyde was obtained as a white powder in 92% yield, m.p. 204°-206°; $[\alpha]_D +4.8°$ (c 1.1, DMSO)

(d) 4-(α-D-mannopyranosyl)-3-methoxy-benzaldehyde was obtained crystalline in 64% yield, m.p. 196°-197° (ethanol), $[\alpha]_D +119.6°$ (c 1, DMSO)

III. Nitromethylation of hydroxy-benzaldehyde glycosides

Both acetylated and deacetylated hydroxy-benzaldehyde glycosides, as prepared above, were next nitromethylated to the corresponding nitrostyryl glycosides.

Nitromethane (16 ml), ammonium acetate (8 g) and acetic acid (4 ml) were added to a stirred solution or suspension of the appropriate glycoside (20 m mole) in ethanol (150-200 ml), and the mixture stirred at room temperature for a period of from about 20 up to about 250 hours, usually about 20 hours. In most cases the product separated from the reaction mixture and was collected from the reaction mixture, though in some cases the product was precipitated by addition of water followed by either filtration or extraction by chloroform or other suitable solvent.

Alternatively the reaction mixture described above was refluxed for 15-45 minutes, affording similar yields of products though often of improved purity.

The results obtained on preparation of various nitrostyryl glycosides are given below, indicating the method used, either method (A), the room temperature method or method (B), the reflux method.

(a) 4-(2-acetamido-3,4,6-tri-O-acetyl-2-deoxy-β-D-glucopyranosyloxy)-3-methoxy-ω-nitrostyrene was prepared in 88% by method (A) and 76% by method (B), as a yellow crystalline solid, m.p. 239°-240°, $[\alpha]_D -6.9°$ (c 1.15, DMSO).

(b) 4-(2-acetamido-2-deoxy-β-D-glucopyranosyloxy)-3-methoxy-ω-nitrostyrene was prepared by method (B) in 87% yield as a pale yellow solid, m.p. 200°-201.5° (dec.), $[\alpha]_D -1.4°$ (c 0.9, DMSO).

(c) 4-(2-acetamido-3,4,6-tri-O-acetyl-2-deoxy-β-D-glucopyranosyloxy)-ω-nitrostyrene was prepared by method (B) as a very pale yellow solid, m.p. 258°-259°, $[\alpha]_D -14.3$ (c 1.1, CHCl$_3$).

(d) 4-(2,3,4,6-Tetra-O-acetyl-β-D-glucopyranosyloxy)-3-methoxy-ω-nitrostyrene was prepared by method (A) as a creamy yellow solid, in 96% yield, m.p. 192°-194° $[\alpha]_D -12.4°$ (c 1.2, CHCl$_3$).

(e) 4-(2,3,4,6-Tetra-O-acetyl-β-D-galactopyranosyloxy)-3-methoxy-ω-nitrostyrene was prepared by method (a) in 25% yield after extraction from the reaction mixture with dichloromethane and chromatography on a silica gel column using ether-light petroleum as eluent. It had m.p. 148°-149° $[\alpha]_D -4.4°$ (c 1.1, CHCl$_3$).

(f) 4-β-D-galactopyranosyloxy-3-methoxy-ω-nitrostyrene was obtained by method (A) as pale yellow crystals in 69% yield, m.p. 212°-214°, $[\alpha]_D +1.3°$ (c 1.5, DMSO).

(g) 4-(2,3,4,5-Tetra-O-acetyl-α-D-mannopyranosyloxy)-3-methoxy-ω-nitrostyrene was obtained by method (A) as a pale yellow amorphous solid, m.p. 131°-132°, $[\alpha]_D -15.7°$ (c 0.8, CHCl$_3$).

IV. O-deacetylation of nitrostyryl glycosides

Finally O-acetylated nitrostyryl glycosides, as prepared above, are deacetylated.

A stirred solution or suspension of the appropriate O-acetylated nitrostyryl glycoside (2 mmole) in methanol (150 ml) was treated with M-methanolic sodium methoxide (2.5 ml). The mixture was stirred at room temperature 10-20 min, and then passed through a wad of silica gel to remove sodium ions. The silica gel was washed well with methanol and the combined filtrate and washings evaporated to dryness. The resulting solid was then filtered off with the aid of a little ethanol. The results obtained for the various nitrostyryl glycosides prepared are given below.

(a) 4-(2-acetamido-2-deoxy-β-D-glucopyranosyloxy)-3-methoxy-ω-nitrostyrene was obtained as a pale yellow amorphous powder in quantitative yield, which could not be recrystallised satisfactorily without causing some decomposition. It had m.p. 198°-199° (dec.), $[\alpha]_D -7.8$ (c 1.4, DMSO).

(b) 4-β-D-glucopyranosyloxy-3-methoxy-ω-nitrostyrene was prepared in 77% yield as yellow crystals, m.p. 140°-141°, $[\alpha]_D -8.7°$ (c 1, DMSO).

(c) 4-α-D-mannopyranosyloxy-3-methoxy-ω-nitrostyrene (23) was obtained as an amorphous hydroscopic orange solid, $[\alpha]_D +80.1°$ (c 0.8, DMSO).

The glycosides prepared above are suitable for use in the detection and determination of the corresponding glycosidases. Reagents comprising these glycosides are included within the invention and may be used in the method of the invention. Typically the glycosides release the corresponding hydroxy-nitrostyryl compound, on interaction with the appropriate enzyme, which provides the easily discernible visual signal, usually a red colouration.

An inert solid phase material may be impregnated with the glycosides prepared above or other enzyme substrates according to the invention. For example, the requisite amount of microcrystalline cellulose (Avicell) is added to the eluate from the silica gel, as prepared above, evaporated to dryness in a rotary evaporator and the resulting solid ground to a fine powder with a mortar and pestle.

EXAMPLE 2

Preparation of Ester Derivations of 4-hydroxy-ω-nitrostyrenes for Detection and Determination of corresponding Esterases A range of ester derivatives of the 4-hydroxy-ω-nitrostyrenes was prepared for use in reagents according to the invention for detection and determination of corresponding esterases.

(1) 4-Acetoxy-3-methoxy-ω-nitrostyrene

Vannillyl acetate (19.4 g, 100 mmole) was reacted with nitromethane, ammonium acetate and acetic acid, as in method A part III of Example 1, for a period of 2-3 days. The red coloured reaction mixture was then diluted with water and the resultant oil layer extracted with chloroform. The chloroform extract was dried (MgSO$_4$) and evaporated to dryness, and the resulting solid recrystallised from chloroform-ethanol to give the acetate, m.p. 158°-162.2°, (20 g, 17%).

Alternatively the 3-methoxy-ω-nitrostyryl acetate was prepared from the corresponding hydroxy-nitrostyrene. 4-hydroxy-3-methoxy-ω-nitrostyrene (15 g, 0.77 mmole) was added to acetic anhydride (15 ml) and the mixture heated under reflux for 1½ h. The mixture was then poured into ice-water and the precipitated solid filtered off and recrystallised from chloroform-ethanol to give the acetate (1.7 g, 93%), m.p. 163°–165° identical to that prepared above.

The above ω nitrostyryl acetate is suitable for use in reagents and the method of the invention for detection and determination of acetate esterases, and on interaction with such enzymes gives rise to the release of 4-hydroxy-3-methoxy-ω-nitrostyrene which exhibits a strong red colouration under alkaline conditions.

(2) 4-Propyloxy-3-methoxy-ω-nitrostyrene 4-hydroxy-3-methoxy-ω-nitrostyrene (3.9 g, 20 mmole) was dissolved in dry pyridine (15 ml) and propionyl chloride (2.8 g, c 30 mmole) added. The reaction mixture became warm and a dark red precipitate was formed. After ca 5 min. the mixture was poured into ice-water and the resulting yellow precipitate filtered off, washed well with ethanol and recrystallised from chloroform-ethanol to give the propionate (4.8 g, 95%), m.p. 101°–104.5°. The propionate is suitable for use in the detection of propionate esterases and similarly give rise to the formation of the 4-hydroxy-3-methoxy-ω-nitrostyrene on interaction with the enzyme.

(3) 4-(β-nitroethenyl)-3-methoxyphenyl palmitate 4-hydroxy-3-methoxy-ω-nitrostyrene (5.2 g, 25 mmole) was dissolved in pyridine (20 ml) and palmitoyl chloride (8 g, 29 mmole) added. A yellow solid was formed immediately and the reaction mixture was then heated at reflux for c 5 min; the reaction mixture was poured into ice-water and the resulting yellow solid filtered off. The product was stirred with dilute ($10^{-4}$ molar) sodium hydroxide to remove free phenol, filtered off, washed well with water and ethanol, and then recrystallised from chloroform-ethanol, m.p. 96°–99° (9.1 g, 84%). This product is suitable for use in the detection and determination of palmitate esterases, releasing 4-hydroxy-3-methoxy-nitrostyrene on interaction with the enzyme.

(4) 4-(β-nitroethenyl)-phenyl palmitate

Palmitoyl chloride (3.6 g) was added to dry pyridine (20 ml); there was an immediate precipitation. To this mixture was added 4-hydroxy-ω-nitrostyrene (1.65 g, 10 mmole) and the mixture heated at reflux for 1–2 min. The mixture was then poured into ice-water and the yellow amorphous precipitate filtered off. A solution of the precipitate in a mixture of chloroform and DMSO afforded seed crystals of the ester and the bulk was crystallised by dissolving in boiling methylene chloride and adding ethanol. When all the methylene chloride had evaporated, the ethanolic solution was seeded and gave the palmitate as pale fawn crystals, m.p. 83°–84° (2 g, 50%). Similarly this product is suitable for detection and determination of palmitate esterases, though releases the 4-hydroxy-ω-nitrostyrene on interaction with the enzyme.

(5) 4-(β-nitroetheny)-3-methoxyphenyl phosphate (as monosodium salt mono hydrate)

To vigorously stirred ice-cooled solution of phosphoryl chloride (6.2 g, 40 mmole) in pyridine (40 ml) was added dropwise over 45 min a solution of 4-hydroxy-3-methoxy-ω-nitrostyrene (7.8 g, 40 mmole) in pyridine (20 ml). The reaction mixture was then decomposed by the dropwise addition of aqueous pyridine (50 ml, containing 10% water) during which some solid separated. Dropwise addition of 2 M-sodium hydroxide (20 ml, 40 mmole) initially resulted in a clear solution, followed the separation of an amorphous mono sodium salt, as the hydrate (7.1 g, 59%), m.p.>250°. The salt had a low solubility in water, and is suitable for detection and determination of phosphatases.

(6) 4-(β-nitroethenyl)-3-methoxyphenyl phosphate (as its disodium salt).

The above reaction (5) is repeated except that the decomposed reaction mixture was poured into a concentrated solution of caustic soda (6 g) in water. The product initially separated out as an oil which solidified to an amorphous solid (11 g, 86%) m.p.>250°. It was more soluble in water than the monosodium salt and dissolved easily in boiling water, with a little decomposition, and reprecipitated on cooling to give a pale yellow solid. A 2 mmolar solution of the disodium salt could be made readily.

EXAMPLE 3

A range of hydroxy-ω-nitrostyrenes was also prepared to determine and compare the colour properties of these compounds, being examples of compounds falling within the general formula X—A—Y—NO$_2$ i.e. compounds which may be formed as a result of interaction of the reagent of the invention with the corresponding enzyme.

The general preparative procedure used was as follows. The corresponding hydroxybenzaldehyde (40 mmole) was dissolved in ethanol (200 ml) and ammonium acetate (12 g), nitromethane (32 ml) and acetic acid was added. The reaction mixture was either stirred overnight at room temperature or heated under reflux for 15–60 minutes. In some cases the ω-nitrostyrene crystallised from the cooled reaction mixture, or crystallised when water was added to the cooled reaction mixture. In cases where no crystalline product could be isolated by these methods, the product was extracted with ether, which was washed well with water, dried (MgSO$_4$) and taken to dryness. The yields, melting points and spectral properties of the various hydroxy-ω-nitrostyrene products were determined by conventional methods and are given below, the spectral properties being determined in terms of the absorbance (λmax) in ethanol and TRIS buffer of pH 8.8 and the extinction coefficient ($\epsilon$) at pH 8.8.

(1) 4-hydroxy-3-methoxy-ω-nitrostyrene had m.p. 164°–166° C. (ethanol), was obtained in 75% yield, and had λ max (ethanol) of 380 and λ max (TRIS 8.8) of 506 with $\epsilon$ 20,900.

(2) 4-hydroxy-ω-nitrostyrene had m.p. 185°–186° (aqueous ethanol), was obtained in 52% yield, and had λ max (ethanol) of 358 and λ max (TRIS 8.8) of 460 with $\epsilon$ of 24,627.

(3) 4-hydroxy-3,5-dimethoxy-ω-nitrostyrene had m.p. 184°–186° (ethanol), was obtained in 72% yield, and had λ max (ethanol) of 385 and λ max (TRIS 8.8) of 530 with $\epsilon$ of 22,330.

(4) 4-hydroxy-3-nitro-ω-nitrostyrene had m.p. 132°–133°, was obtained in 57% yield, and had λ max (ethanol) of 320 and λ max (TRIS 8.8) of 405 with $\epsilon$ of 7,400.

(5) 4-hydroxy-3-methoxy-2-nitro-ω-nitrostyrene had m.p. 188°–189° (aqueous acetic acid) was obtained in 42% yield, and had λ max (ethanol) of 400 and λ max (TRIS 8.8) of 436 with $\epsilon$ of 14,000.

(6) 4-hydroxy-3-methoxy-5-nitro-ω-nitrostyrene had m.p. 170°–171° (aqueous acetic acid), was obtained in 67% yield and had λ max (ethanol) of 334 and λ max (TRIS 8.8) of 415 with $\epsilon$ of 5,200.

(7) 2-hydroxy-3-methoxy-ω-nitrostyrene had m.p. 138°–139° (aqueous ethanol), was isolated in 38% yield and had λ max (ethanol) of 322 and λ max (TRIS 8.8) of 492 with extinction coefficient ε of 7,380.

2-methoxy-4-(α-methyl-β-nitroethenyl)-phenol was also prepared by a variation of the above procedure in which vanillin was treated with nitroethane instead of nitromethane. The conditions employed for the reaction, however, were essentially the same as those described above for nitromethylation. The α-methyl-β-nitroethenyl phenol product was obtained in 80% yield with m.p. 110°–112° and had λ max (ethanol) of 368 and λ max (TRIS 8.8) of 475 with ε of 13,100.

The hydroxy ω-nitrostyrenes, as prepared above, are typically coloured compounds which may provide the easily discernible visual signal of the reagents of the invention. Particularly preferred compounds are the 3-methoxy and 3,5-dimethoxy compounds, 1 and 3, which provides distinctive, deep red colourations under alkaline conditions. Generally, the ω-nitrostyrene compounds exhibit markedly improved colour properties over the pale orange-yellow colouration of paranitrophenol (λ max ethanol 320, λ max TRIS 8.8 400 with ε of 15,000), which it is believed is due to the formation radical ions with the nitrostyryl compounds. The existence of such radical ions is supported by the e.s.r. spectra of the nitrostyryl compounds. For example, the 3,5-dimethoxy compound (3), in solution in DMSO to which one drop of M sodium methoxide has been added, gave a strong e.s.r. spectrum comprising 7 signals for the six methoxy protons in the ratio 1:6:15:20:15:6:1 with a calculated splitting of 0.680 gauss, and 3 signals for the two aromatic protons in the ratio 1:2:1 with a calculated splitting of 1.74 gauss, no signals being observed for the ethyl protons.

EXAMPLE 4

Assay for N-Acetylglucosaminidase (NAG) in urine 100 mg of microcrystalline cellulose containing about 3% of the 4-(2-acetamido-2-deoxy-β-D-glucopyranosyloxy)-3-methoxy-ω-nitrostyrene, the substrate for NAG, as prepared in Example 1, is treated in a small plastic sample tube with fresh urine (1 ml) at body temperature, or stored urine pre-heated to 35°–38° C. The contents of the tube are incubated for 15–30 minutes at 30°–35° C. e.g. 20 minutes at 37° C., and then allowed to percolate through a short column (about 3×0.6 cm) of fibrous DEAE cellulose (Whatman DE22) contained in a Pasteur pipette blocked at the bottom with cotton wool. The presence of NAG in the urine sample is indicated by the development of a crimson red band about 0.5 cm. below the top of the DEAE cellulose column. Sometimes a broad light brown band forms above the crimson red band due to urochrome present in the urine, and in a few patients who have had kidney transplants a fast moving brown-mauve band is observed probably due to the medication the patient is receiving. Further, for diabetics or infants, who have low electrolyte concentrations in their urine, the red band forms at the top surface interface of the DEAE cellulose and is more dispersed in nature. This latter effect can be overcome by incorporation of appropriate quantities of electrolytes into the reagent. In all cases, however, the width and intensity of the red band is approximately proportional to the concentration of NAG in the urine.

Using 3% glycoside on cellulose, normal urine (about 40–75 n mol/ml of NAG) gave a narrow faint compact red band, but abnormal urines (>200 n mol/ml NAG) gave intense broader bands which intensified with increasing NAG concentrations. Under the same conditions of testing, water and urine which has been boiled to destroy NAG, gave negative results.

In a modification of the basic assay, 8% glycoside on cellulose is used in place of the 3% glycoside material, and estimated to have a NAG detection threshold of from about 20–30 n mol/ml. In the modified procedure normal urine gives more intense bands than are observed above indicating the way in which it is possible to choose a threshold of detection by variation of the quantity of glycoside substrate used, and also paying attention to the temperature and time of incubation.

DESCRIPTION OF A THROUGH-FLOW DEVICE ACCORDING TO THE INVENTION

With reference to FIGS. 1 and 2 the ω-nitrostyrylglycosides, as prepared in Example 1, may be incorporated into through-flow devices according to the invention. Both devices comprise cylindrical upper incubation 1 and lower visualisation 2 compartments, and in both cases the lower visualisation compartment 2 contains a quantity of fibrous DEAE cellulose (Whatman DE 22) 3 sandwiched between upper 4 and lower 5 layers of cotton wool or a similar substance. The lower ends of the visualisation compartments 2 have outlets 6 for draining of fluid and are provided with a skirt or legs 7 to allow free standing of the devices in a vertical orientation. The walls of the lower visualisation compartments 2 are of clear material, such as clear plastic, to permit observation of the DEAE cellulose and any coloured band absorbed thereon.

The upper incubation compartments 1 contain an appropriate quantity of the glycoside substance (not shown) either in a suitable solvent or absorbed into cellulose or other suitable absorbent e.g. 100 mg of microcrystalline cellulose (Avicell) containing 3% glycoside. The incubation compartments 1 are fitted with screw caps and have thick PVC or polystyrene walls 9 to insulate the urine during incubation, the walls 9 being marked with a line 10 to indicate the quantity of urine which is to be introduced for incubation.

In diagram, FIGS. 1 and 2, the upper and lower compartments 1 and 2 are shown without a connecting passageway between them.

With reference to FIG. 1, the compartments 1 and 2 are held together at interfacial surfaces by pivot pin 11. The base of incubation compartment 1 has an eccentrically located outlet 12 and the top of the visualisation compartment has an inlet 13 eccentrically located at the same radius from the pivot 11 as outlet 12. Mutual rotation of the upper 1 and lower 2 compartments brings the outlet 12 and inlet 13 into coincidence with one another providing a passageway connecting the compartments through which incubated urine can flow. In use, fresh urine is introduced into compartment 1 up to the level of the mark 10, outlet 12 and inlet 13 being out of coincidence with one another. The screw cap 8 is screwed in place and the urine is incubated for a period which depends upon the temperature, though is usually about 15 to 20 minutes. The compartments are then mutually rotated bringing outlet 12 and inlet 13 into register with one another and incubated urine drains from the incubation compartment 1 to the visualisation compartment 2. 2-methoxy-4-(2-nitro-(E)-ethenyl) phenol released by the glycoside substrate as a result of NAG present in the urine gives rise to the formation of a bright scarlet red band about 0.5 cm below the top of the DEAE cellulose column 3.

With reference to FIG. 2, compartments 1 and 2 are held together in screw-threaded engagement by screw thread 16 around the bottom of compartment 1 and screw thread 17 around the inside of tubular extension 18 projecting from the top of compartment 2. A passageway between compartments 1 and 2 is provided by tubular extension 14 which projects from the bottom of compartment 1. Prior to use passageway 14 is closed by its abutment with the weakened section 15 in the top of compartment 2. In use, urine is introduced to compartment 1 and incubated as for the device of FIG. 1. On completion of incubation, however, compartments 1 and 2 are screwed together and the tubular extension 14 breaks through the weakened section 15 permitting incubated urine to flow into compartment 2. Visualisation of the phenol released by the substrate is as for the device of FIG. 1.

Both devices provide simple means by which "kidney transplant" patients may test themselves in their own homes, or general screening tests may be easily conducted, without access to sophisticated monitoring apparatus. Other enzymes besides NAG may be assayed using similar techniques and devices.

We claim:

1. An enzyme substrate of formula S'—X—A—Y—NO$_2$, wherein A represents an aromatic nucleus, X represents an auxochromic radical, Y represents an unsaturated group which is capable of transmitting electron resonance between the aromatic nucleus A and the nitro (NO$_2$) substituent, and S' is selected from the group consisting of propionyloxy, palmitoyloxy, phosphate, diphosphate, sulfate, and glycosyl residue.

2. An enzyme substrate according to claim 1, wherein S' is a β-glucopyranosyl, galactopyranosyl, or mannopyranosyl glycoside, for assay of a corresponding glycosidase enzyme.

3. An enzyme substrate according to claim 2, wherein S' is 2-acetamido-2-deoxy-β-D-glucopyranosyl glycoside for assay of N-acetyl-β-D-glucosaminidase enzyme.

4. An enzyme substrate according to any of claims 1–3, in which A represents a benzene nucleus.

5. An enzyme substrate according to claim 4 which has formula I:

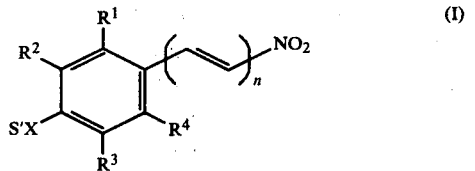

wherein n is 1, 2 or 3; $R^1$, $R^2$, $R^3$ and $R^4$ are the same or different and selected from the group consisting of H, Me, NO$_2$, CH$_3$, CH=CR'R", and CO$_2$H; wherein R' and R" are the same or different and selected from the group consisting of H, Me, NO$_2$, CH$_3$, CO$_2$H and further conjugated substituent of formula CH=CR'R".

6. An enzyme substrate according to any of claims 1–3, wherein said auxochromic radical X comprises an amino (—NH—) or a hydroxyl (—O—) radical.

7. An enzyme substrate according to any of claims 1–3 which on interaction with the enzyme releases the compound 4-hydroxy-3-methoxy-ω-nitrostyrene or 4-hydroxy-3,5-dimethoxy-ω-nitrostyrene.

8. A product comprising a substrate according to any of claims 1–3 in combination with an insoluble solid phase material.

9. A product according to claim 8 in which the solid phase material is in the form of a test paper or dip stick.

10. A process for the production of an enzyme substrate of formula:

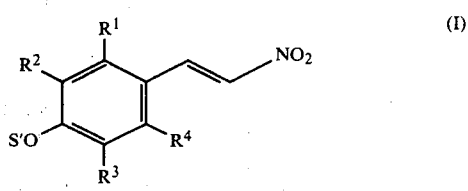

wherein S' is selected from the group consisting of propionyloxy, palmitoyloxy, phosphate, diphosphate, sulfate, and glycoside residue; wherein $R^1$, $R^2$, $R^3$ and $R^4$ are the same or different and selected from the group consisting of H, Me, NO$_2$, CH$_3$, CH=CR'R", and CO$_2$H; wherein R' and R" are the same or different and selected from the group consisting of H, Me, NO$_2$, CH$_3$, CO$_2$H, and further conjugated substituent of formula CH=CR'R", which comprises:

reacting a hydroxy benzaldehyde compound starting material with an appropriate enzyme substrate residue S', to give the corresponding enzyme substrate residue-hydroxy benzaldehyde compound adduct, and then nitromethylating said adduct.

11. A method for the assay of an enzyme which comprises:

incubating a sample containing said enzyme with a reagent comprising a substrate for said enzyme which reacts with said enzyme to give rise to the formation of a compound which is monitored, wherein said substrate has the formula S'—X—A—Y—NO$_2$, and said monitored compound has the formula HX—A—Y—NO$_2$, wherein S' comprises the enzyme substrate portion of the reagent, A represents an aromatic nucleus, HX represents an auxochromic group and Y represents an unsaturated group which is capable of transmitting electron resonance between the aromatic nucleus (A) and the nitro substituent (NO$_2$), said monitored compound being capable of producing a visual signal which is discernable by eye either directly or on alkaline treatment.

12. A method according to claim 11 for the assay of a carboxylate, esterase or lipase, an acid or alkaline phosphatase, phosphodiesterase, a sulfatase or a glycosidase enzyme, wherein said enzyme substrate has formula S'—X—A—Y—NO$_2$, wherein X represents an auxochromic radical corresponding to an auxochromic group HX as hereinbefore defined, and S' represents a carboxylate, phosphate, diphosphate, sulfate or glycosyl residue.

13. A method according to claims 11 or 12 wherein said monitored compound has formula I

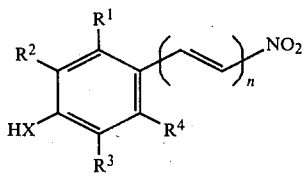

(I)

wherein HX is an auxochromic group; n is 1, 2 or 3; $R^1$, $R^2$, $R^3$ and $R^4$ are the same or different and selected from the group consisting of H, Me, $NO_2$, $CH_3$, CH=CR'R", and $CO_2H$; wherein R' and R" are the same or different and selected from the group consisting of H, Me, $NO_2$, $CH_3$, $CO_2H$, and further conjugated unsaturated substituent of formula CH=CR'R".

14. A method according to claims 11 or 12 in which sample and reagent are incubated together at a temperature greater than 30° C. for a period of up to 30 minutes.

15. A method according to claims 11 or 12, in which the reagent is used in association with an insoluble solid phase material.

16. A method according to claims 11 or 12, wherein a solution containing the compound of formula HX—A—Y—$NO_2$ is brought into contact with a solid phase reagent which presents an alkaline environment to said compound.

17. An apparatus for the assay of an enzyme in the form of a flow-through device which comprises:
an incubation compartment;
a visualization compartment;
an outlet in said incubation compartment interconnectable to an inlet in said visualization compartment;
said incubation compartment containing a reagent comprising a substrate for said enzyme which reacts with said enzyme to give rise to the formation of a compound which is monitored, wherein said substrate has the formula S'—X—A—Y—$NO_2$, and said monitored compound has the formula HX—A—U—$NO_2$, wherein S' represents the enzyme substrate portion of the reagent, A represents an aromatic nucleus, X represents an auxochromic group, and Y represents an unsaturated group which is capable of transmitting electron resonance between the aromatic nucleus (A) and the nitro substituent ($NO_2$), said monitored compound being capable of producing a visual signal which is discernable by eye directly or on alkaline treatment;
said visualization compartment containing a solid phase reagent which presents an alkaline environment to said monitored compound of formula HX—A—Y—$NO_2$.

18. The apparatus of claim 17 wherein said incubation and visualization compartments are held together by a screw threaded engagement.

19. The apparatus of claim 17 wherein said incubation and visualization compartments are held together by pivotable means.

20. The apparatus of any of claims 17, 18 or 19 wherein said substrate for said enzyme has the formula S'X—A—Y—$NO_2$;
wherein X represents an auxochromic radical corresponding to said auxochromic group XH, and S is selected from the group consisting of propionyloxy, palmitoyloxy, phosphate, diphosphate, sulfate and glycosyl residue.

21. The apparatus of claim 20 wherein said substrate has formula:

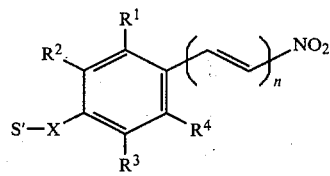

(I)

wherein n is 1, 2 or 3; $R^1$, $R^2$, $R^3$ and $R^4$ are the same or different and selected from the group consisting of H, Me, $NO_2$, $CH_3$, CH=CR'R", and $CO_2H$; wherein R' and R" are the same or different and selected from the group consisting of H, Me, $NO_2$, $CH_3$, $CO_2H$, and further conjugated substituent formula CH=CR'R".

22. The apparatus of claims 17, 18 or 19 wherein said substrate of said enzyme in said incubation compartment is in combination with a solid phase material.

* * * * *

UNITED STATES PATENT AND TRADEMARK OFFICE
CERTIFICATE OF CORRECTION

PATENT NO. : 4,318,986
DATED : March 9, 1982
INVENTOR(S) : ANTHONY C. RICHARDSON ET AL It is certified that error appears in the above—identified patent and that said Letters Patent is hereby corrected as shown below:

Please correct the inventors information as follows:

[75] -- Inventors:

Anthony C. Richardson, Henley-on-Thomas;

Percy F.G. Praill, Uxbridge;

Robert G. Price, Northwood, all of England --.

Signed and Sealed this

Twenty-first Day of December 1982

[SEAL]

Attest:

GERALD J. MOSSINGHOFF

Attesting Officer    Commissioner of Patents and Trademarks